US009155631B2

(12) United States Patent
Seifert et al.

(10) Patent No.: US 9,155,631 B2
(45) Date of Patent: Oct. 13, 2015

(54) INTERVERTBRAL IMPLANT

(75) Inventors: Jody L. Seifert, Birdsboro, PA (US);
Michal Zentko, Bryn Mawr, PA (US);
Andrew Iott, Villanova, PA (US);
Christopher Angelucci, Schwenskville, PA (US); Chad Glerum, Pennsburg, PA (US); Ryan Watt, Boyertown, PA (US)

(73) Assignee: GLOBUS MEDICAL INC., Audubon, PA (US)

( * ) Notice: Subject to any disclaimer, the term of this patent is extended or adjusted under 35 U.S.C. 154(b) by 318 days.

(21) Appl. No.: 12/756,438

(22) Filed: Apr. 8, 2010

(65) Prior Publication Data
US 2011/0251689 A1 Oct. 13, 2011

(51) Int. Cl.
*A61F 2/44* (2006.01)
*A61B 17/86* (2006.01)
*A61F 2/30* (2006.01)
*A61F 2/46* (2006.01)
*A61F 2/28* (2006.01)

(52) U.S. Cl.
CPC ............... *A61F 2/447* (2013.01); *A61F 2/442* (2013.01); *A61B 17/86* (2013.01); *A61F 2/30* (2013.01); *A61F 2/4684* (2013.01); *A61F 2002/2835* (2013.01); *A61F 2002/3008* (2013.01); *A61F 2002/3081* (2013.01); *A61F 2002/30401* (2013.01); *A61F 2002/30482* (2013.01); *A61F 2002/30494* (2013.01); *A61F 2002/30504* (2013.01); *A61F 2002/30507* (2013.01); *A61F 2002/30517* (2013.01); *A61F 2002/30522* (2013.01); *A61F 2002/30578* (2013.01); *A61F 2002/30604* (2013.01); *A61F 2002/30808* (2013.01); *A61F 2002/30843* (2013.01); *A61F 2002/30878* (2013.01); *A61F 2002/4475* (2013.01); *A61F 2310/00023* (2013.01)

(58) Field of Classification Search
CPC ...... A61F 2/4455; A61F 2/4465; A61F 2/442; A61F 2/447; A61F 2002/4475
USPC ............................................. 623/17.11–17.16
See application file for complete search history.

(56) References Cited

U.S. PATENT DOCUMENTS

| 5,397,364 | A | 3/1995 | Kozak |
| 6,342,074 | B1 | 1/2002 | Simpson |
| 6,485,517 | B1 | 11/2002 | Michelson |
| 6,558,423 | B1 | 5/2003 | Michelson |
| 6,716,247 | B2 | 4/2004 | Michelson |

(Continued)

FOREIGN PATENT DOCUMENTS

WO WO 2007/098288 8/2007

*Primary Examiner* — Christopher Beccia
*Assistant Examiner* — Diana S Jones

(57) ABSTRACT

The present invention provides an intervertebral implant for implantation in a treated area of an intervertebral space between vertebral bodies of a spine. The implant includes a spacer portion having an inferior and superior surface, wherein the inferior and superior surfaces each have a contact area capable of engaging with anatomy in the treated area, and the inferior and superior surfaces define a through-hole extending through the spacer body. The present invention further provides screw holes extending from a side portion to the inferior and superior surfaces of the spacer portion and a plate portion rigidly coupled to the spacer portion through a coupling means, wherein the plate portion contains screws holes for receiving screws. A screw back out prevention mechanism adapted on the plate portion to prevents the back out of screws from the screw holes and to secure the spacer portion to the plate portion of the intervertebral implant.

20 Claims, 6 Drawing Sheets

(56) References Cited

U.S. PATENT DOCUMENTS

| | | |
|---|---|---|
| 6,749,636 B2 | 6/2004 | Michelson |
| 6,800,092 B1 * | 10/2004 | Williams et al. ............ 623/17.11 |
| 6,890,355 B2 | 5/2005 | Michelson |
| 6,984,234 B2 | 1/2006 | Bray |
| 7,033,394 B2 | 4/2006 | Michelson |
| 7,041,135 B2 | 5/2006 | Michelson |
| D530,423 S | 10/2006 | Miles |
| 7,192,447 B2 | 3/2007 | Rhoda |
| 7,232,463 B2 | 6/2007 | Falahee |
| 7,238,203 B2 | 7/2007 | Bagga |
| 7,435,262 B2 | 10/2008 | Michelson |
| 7,442,209 B2 | 10/2008 | Michelson |
| 7,455,692 B2 | 11/2008 | Michelson |
| 7,674,297 B2 | 3/2010 | Falahee |
| 7,972,363 B2 | 7/2011 | Moskowitz |
| 8,268,000 B2 | 9/2012 | Waugh |
| 8,273,127 B2 | 9/2012 | Jones |
| 8,540,774 B2 * | 9/2013 | Kueenzi et al. ............ 623/17.16 |
| 2006/0085071 A1 * | 4/2006 | Lechmann et al. ........ 623/17.11 |
| 2007/0233523 A1 | 10/2007 | Izumi |
| 2007/0293848 A1 | 12/2007 | Endo |
| 2008/0183293 A1 | 7/2008 | Parry |
| 2008/0249575 A1 | 10/2008 | Waugh |
| 2008/0281425 A1 | 11/2008 | Thalgott |
| 2008/0312742 A1 | 12/2008 | Abernathie |
| 2009/0030520 A1 | 1/2009 | Biedermann |
| 2009/0105830 A1 | 4/2009 | Jones |
| 2009/0105831 A1 | 4/2009 | Jones |
| 2009/0182430 A1 | 7/2009 | Tyber |
| 2009/0192613 A1 | 7/2009 | Wing |
| 2009/0210062 A1 | 8/2009 | Thalgott |
| 2010/0057206 A1 * | 3/2010 | Duffield et al. ............ 623/17.16 |
| 2010/0305704 A1 | 12/2010 | Messerli |
| 2014/0148905 A1 | 5/2014 | Messerli |

\* cited by examiner

INTERVERTBRAL IMPLANT

FIELD OF THE INVENTION

The present disclosure generally relates to a fixation device for positioning and immobilizing at least two adjacent vertebra.

BACKGROUND OF THE INVENTION

The vertebral spine is the axis of the skeleton on which all of the body parts "hang". In humans, the normal spine has seven cervical, twelve thoracic and five lumbar segments. The lumbar spine sits upon the sacrum, which then attaches to the pelvis, and in turn is supported by the hip and leg bones. The bony vertebral bodies of the spine are separated by intervertebral discs, which act as joints but allow known degrees of flexion, extension, lateral bending, and axial rotation and translation.

The typical vertebra has a thick anterior bone mass called the vertebral body, with a neural (vertebral) arch that arises from the posterior surface of the vertebral body. The central of adjacent vertebrae are supported by intervertebral discs. The spinal disc and/or vertebral bodies may be displaced or damaged due to trauma, disease, degenerative defects, or wear over an extended period of time. One result of this displacement or damage to a spinal disc or vertebral body may be chronic back pain. In many cases, to alleviate back pain from degenerated of herniated discs, the disc is removed along with all or part of at least one neighboring vertebrae and is replaced by an implant that promotes fusion of the remaining bony anatomy. However, the success or failure of spinal fusion may depend upon several factors. For instance the spacer or implant or cage used to fill the space left by the removed disc and bony anatomy must be sufficiently strong to support the spine under a wide range of loading conditions. The spacer should also be configured so that it likely to remain in place once it has been positioned in the spine by the surgeon. Additionally the material used for the spacer should be biocompatible material and should have a configured that promotes bony ingrowth.

In combination with spacers or cages, a plating system is used to further stabilize the spine during the fusion process. These devices, commonly referred to as bone fixation plating systems, typically include one or more plates and screws for aligning and holding vertebrae in a fixed position with respect to one another. Plating systems independent of the spacers provide additional complications such as loosening and failure of the hardware. Two common failures are the breakage of the plates, and the backing out of screws into soft tissues of the patient's body. The backing out of the screws is typically a result of the screws failure to achieve a sufficient purchase in the bone, although the stripping of the screws has also been known to cause this problem. Another common problems is that plating systems require "carpentry" work to match fit aspects of the vertebral bodies.

There is a need for a spine stabilization system that promotes fusion of adjacent vertebrae while at the same time provides stabilization of the spinal area where fusion occurs. There is a need for a system that incorporates both the fusion element and the plating element in one system to reduce the possible complications that may occur. There is also a need to provide a system that reduces the complications that may occur in the fusion element and the plating element and a need for this system to be configured so that positioning this system is efficient and easy.

SUMMARY OF THE INVENTION

The present invention provides an intervertebral implant for implantation in a treated area of an intervertebral space between vertebral bodies of a spine. The implant includes a spacer portion having an inferior and superior surface, wherein the inferior and superior surfaces each have a contact area capable of engaging with anatomy in the treated area, and the inferior and superior surfaces define a through-hole extending through the spacer body. The present invention further provides screw holes extending from a side portion to the inferior and superior surfaces of the spacer portion and a plate portion rigidly coupled to the spacer portion through a coupling means, wherein the plate portion contains screws holes for receiving screws. A screw back out prevention mechanism is adapted on the plate portion to prevent the back out of screws from the screw holes and to secure the plate portion to the spacer portion.

DETAILED DESCRIPTION OF THE ILLUSTRATED EMBODIMENTS

Embodiments of the disclosure are generally directed to flexible stabilization systems for use with the anterior, anterolateral, lateral, and/or posterior portions of at least one motion segment unit of the spine. The systems of the invention are designed to be conformable to the spinal anatomy, so as to be generally less intrusive to surrounding tissue and vasculature than existing rigid stabilization systems.

Certain embodiments may be used on the cervical, thoracic, lumbar, and/or sacral segments of the spine. For example, the size and mass increase of the vertebrae in the spine from the cervical to the lumbar portions is directly related to an increased capacity for supporting larger loads. This increase in load bearing capacity, however, is paralleled by a decrease in flexibility and an increase in susceptibility to strain. When rigid immobilization systems are used in the lumbar segment, the flexibility is decreased even further beyond the natural motion restriction of that segment. Replacing the conventional rigid immobilization systems with certain embodiments disclosed herein may generally restore a more natural movement and provide added support to the strain-susceptible area.

Figure 1:
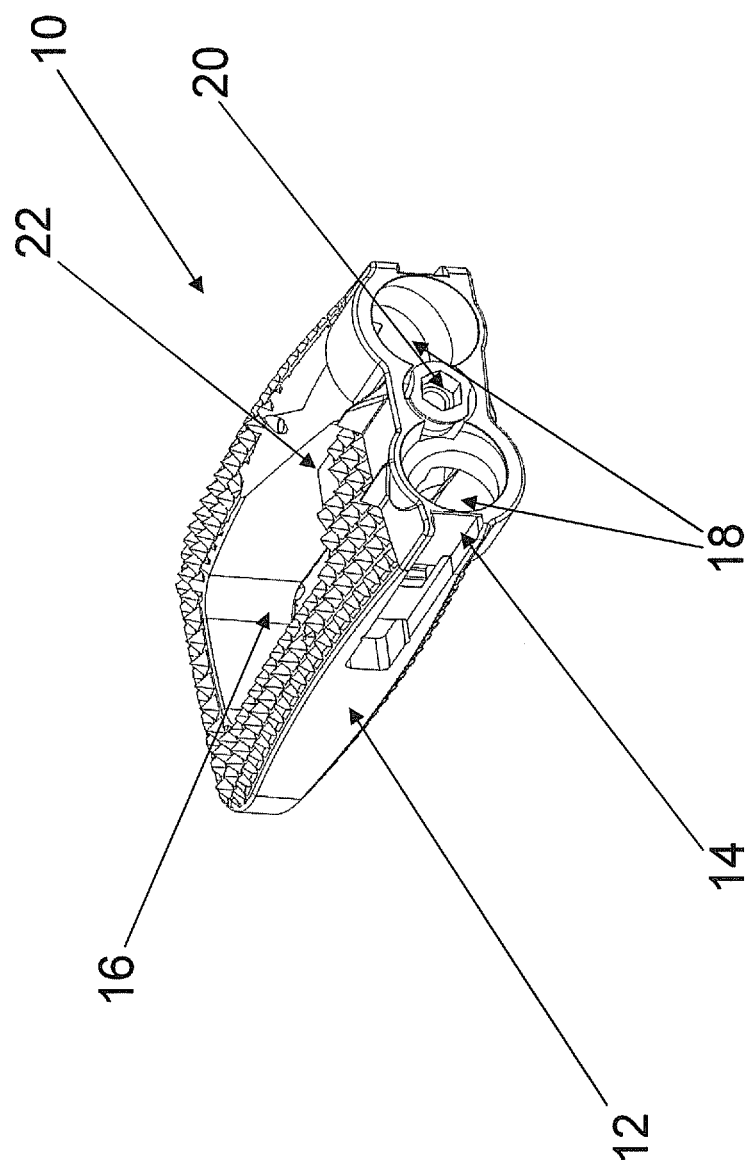
FIG. 1 is a perspective view of one embodiment of an intervertebral implant according to the present invention.

FIGS. 1-4 illustrate the different views of one particular embodiment of the present invention. The intervertebral fusion implant according to the present invention is a standalone interbody fusion device used to provide structural stability in skeletally mature individuals following discectomies. These implants are available in various heights and geometric options to fit the anatomically needs of a wide variety of patients. As shown in FIG. 1, implant 10 is generally positioned in the intervertebral space between two adjacent vertebrae. Implant 10 primarily incorporates a spacer portion 12 and a plate portion 14. In this particular embodiment, the spacer portion 12 includes a graft window 16 for the placement of bone graft to enhance fusion between two adjacent vertebrae. The plate portion 14 includes at least one screw hole 18, however, in the preferred embodiment of the present invention, two screw holes 18 are provided. Also, in the plate portion 14 of the implant 10, pin screw 20 is provided. There is also provided a nut 22 which receives the pin screw 20 to secure the spacer portion 12 and the plate portion 14 rigidly to each other. Although a pin screw and a nut are utilized as a blocking mechanism and a plate and spacer attachment mechanism, any other similar type of arrangement can be also utilized.

It should be noted that the titanium plate portion 14 and the spacer portion 12 maybe coupled through any other feasible means such as hooks, screws, and any other type of fastening means. The implant 10 also allows for at least two titanium screws to be inserted at a compound angle for maximum screw purchase into the superior and inferior vertebral bodies. The pin screw 20 is provided on the plate portion 14 to capture the sides of both of the at least two screws preventing the titanium screws from backing out. It should be noted that the present application is not limited to being of a PEEK spacer and a titanium plate. Other materials that are physiologically compatible which are similar and which may be unique to spacers and plates may be utilized in various combinations.

Figure 2:
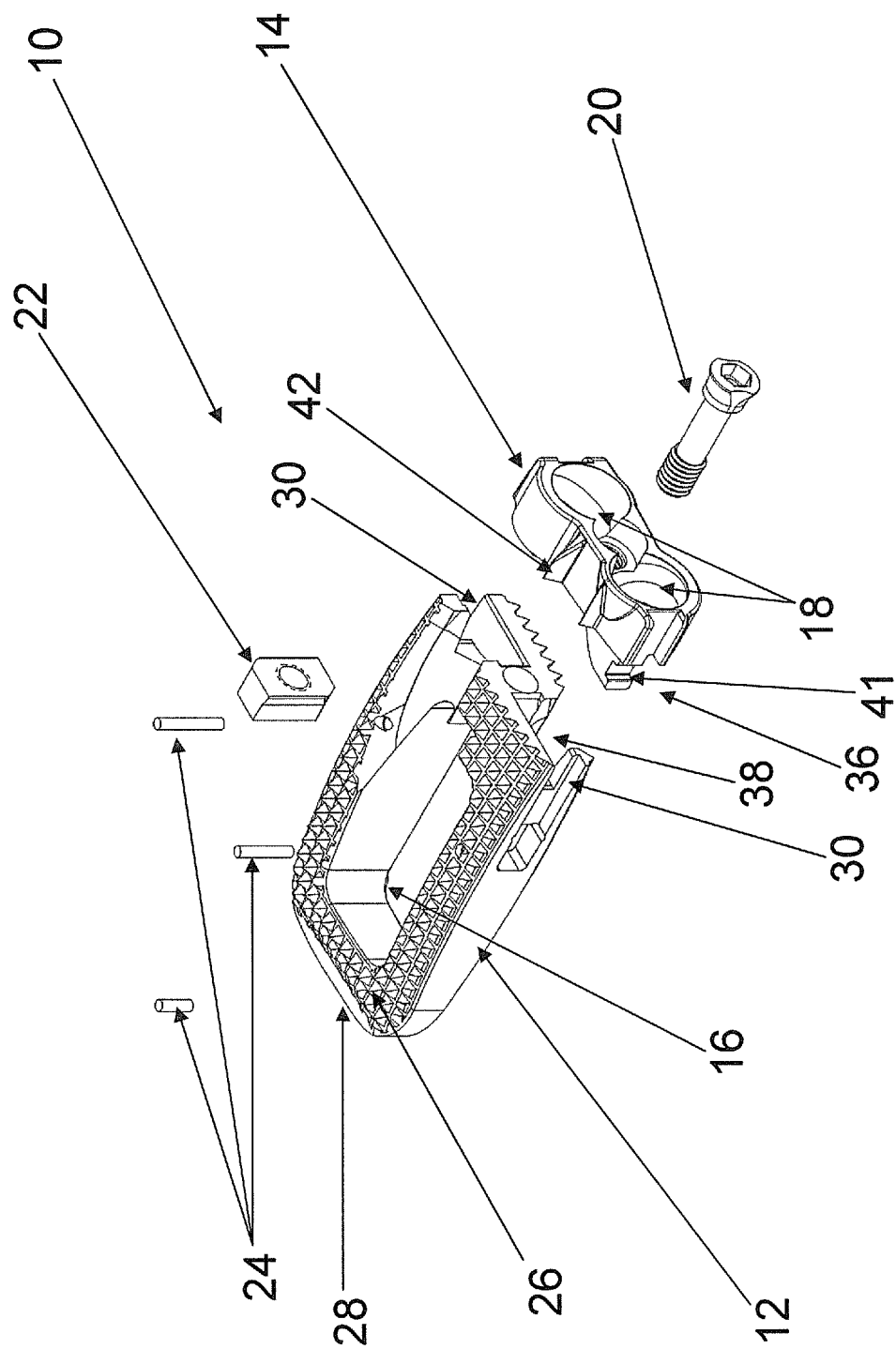
FIG. 2 is an exploded view of the embodiment of the implant shown in FIG. 1.
Figure 3:
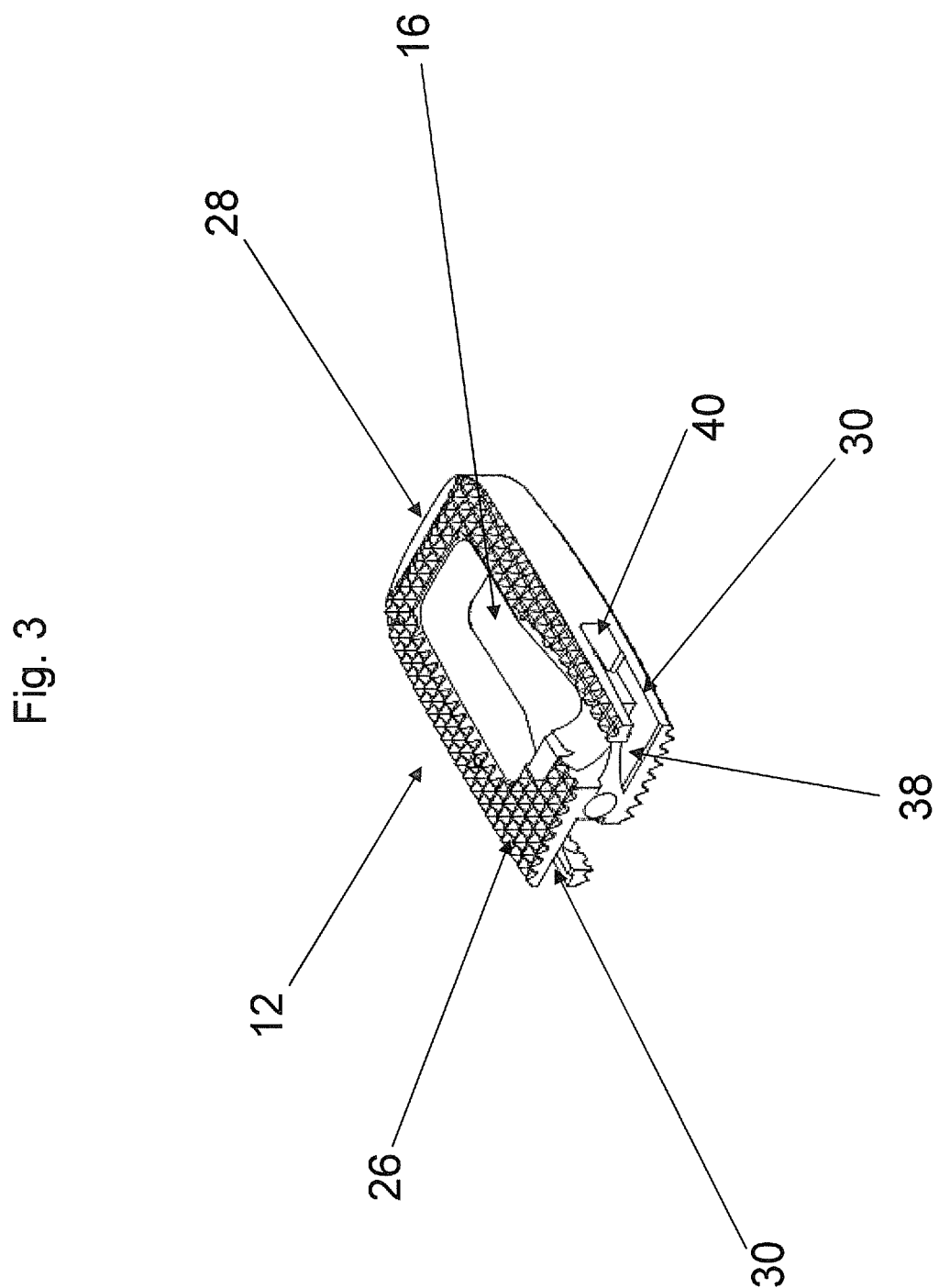
FIG. 3 is a perspective view of the spacer portion of the intervertebral implant of FIG. 1.

In FIGS. 2 and 3, an exploded view of the intervertebral implant 10 and the spacer portion 12 are illustrated in greater detail. The implant 10 comprises the spacer portion 12, plate portion 14, and a pin screw 20 which prevents the back out of the screws as well as securing the plate portion 14 to the spacer portion 12. The spacer portion 12 can be comprised of any material that is conducive to the enhancement of fusion between the two adjacent vertebrae. In one particular embodiment, the spacer portion 12 is made of PEEK material which is physiologically compatible. It should be noted that any other material that are physiologically compatible may also be used. The spacer portion 12 contains tantalum pins 24 that enable radiographic visualization. The spacer portion 12 further comprises superior and inferior portions that are provided with a plurality of pyramidal protrusions 26. The superior and inferior portions of the spacer portion 12 are bi-convex for greater contact with the vertebral endplates of the adjacent vertebrae. The protrusions 26 can be configured to, be any size or shape for further anchoring the spacer portion 12 to each of the adjacent vertebrae. Protrusions 26 on the superior and inferior surfaces of each implant grip the endplates of the adjacent vertebrae to aid in expulsion resistance. Although the protrusions 26 of the preferred embodiment are illustrated as being pyramidal, it should be noted that the protrusions 26 may be designed and configured to be any size and shape that further anchors the implant to the adjacent portions of the vertebrae. The spacer portion 12 of the implant also provides a leading edge chamfer 28 which enables self distraction of the vertebral bodies while inserting. It should be further noted that although FIGS. 1-4 illustrate a spacer portion that is elongated so that the implant may be positioned during an lateral access procedure, the spacer portion can be designed and configured to be in shape and configuration for accessing the spine through any access procedure such as an anterior, posterior and/or transforaminal.

The spacer portion 12 is designed and configured to receive a instrument for positioning the implant 10 into the spine. Cutouts 30 are configured on the outer opposing sides of the spacer portion 12. It should be noted that the length and depth of the cutouts are optimally configured to rigidly hold the implant 10 with the instrument with a minimal amount movement when the holder is attached to the implant.

Figure 4:
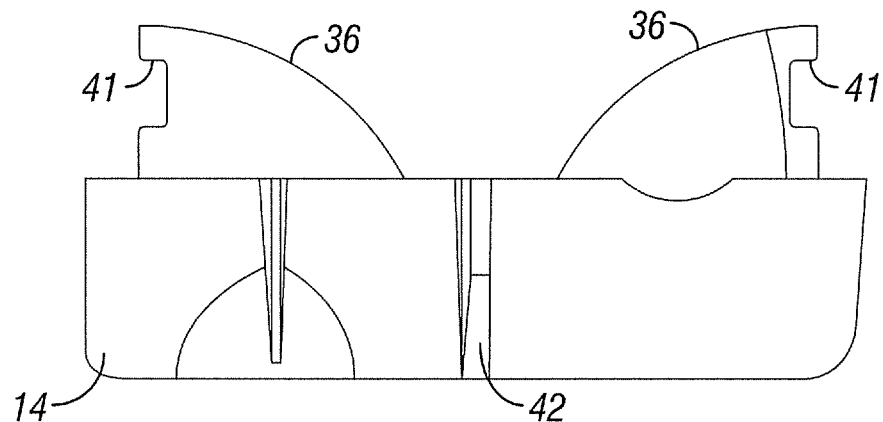
FIG. 4 is a top view of the plate portion of the intervertebral implant of FIG. 1.

Now turning to FIGS. 2 and 4, plate portion 14 will be discussed in greater detail. The plate portion 14 can be comprised of any physiologically compatible material. In the preferred embodiment, the plate portion 14 of the implant 10 is composed of titanium. The plate portion 14 is provided with two screw holes 18. However, it should be noted that implant 10 may be comprised of any amount of screw holes 18. The screw holes 18 are situated both in the spacer portion 12 and the plate portion 14 for receiving bone screws which are attached to the adjacent vertebral bodies at different angles. As shown in FIGS. 2, and 4, the screw holes 18 are configured to receive screws at different angles. One screw hole is configured to direct a bone screw into the superior vertebrae and the a second screw hole is configured to direct a second bone screw into the inferior vertebrae. The screws enter the screw holes 18 at specified angles to enter the adjacent vertebral bodies at the optimal locations. The screws are also configured and adapted to provide optimal purchase with the adjacent vertebral bodies.

The plate portion 14 is further provided with a tongue 36 which couples to a first groove 38 within the cutout of the spacer portion 12. As illustrated in FIG. 4, tongue 36 is curved to correspond to the curvature of the first portion of the groove 38 in the spacer portion 12. A second groove 40 in the spacer portion 12 is also positioned on opposing sides of the spacer portion 12. The second groove 40 is independent of the first groove 38. The second groove 40 is designed and configured to receive a portion of an instrument. The plate portion 14 is also provided with a groove 41 within the tongue 36 which is adapted to couple to the instrument. As a result, the instrument may be used to securely attach the spacer portion 12 and the plate portion 14. It should be noted that although the tongue 36 is provided on the plate portion, in alternative embodiments, the spacer portion may contain a tongue and the plate portion configured to receive the tongue in a groove.

The plate portion 14 is also provided with knife-protrusions 42 positioned on the upper and lower portions of the plate portion 14. These protrusions 42 extend into a portion of the upper and lower vertebrae to help stabilize the implant 10. Specifically, these protrusions 42 enable torsional stability of the implant. The plate 14 is also provided with "eye brow" like structure which fully captures the bone screws while still allowing for the screws to reside about the tooth root plane and remaining lower than the tooth (protrusions on the spacer portion 12). The plate 14 geometry allows for the minimum reduction of peek volume. The plate 14 height remains level to the peek tooth root so that compressive loads are always subjected to the peek body where the graft is contained. Compound holes are drilled to accept bone screws and to allow for fixed or variable angle screws. The anti-back out mechanism is engaged so that the screws do not back out of the implant 10.

Figure 5:
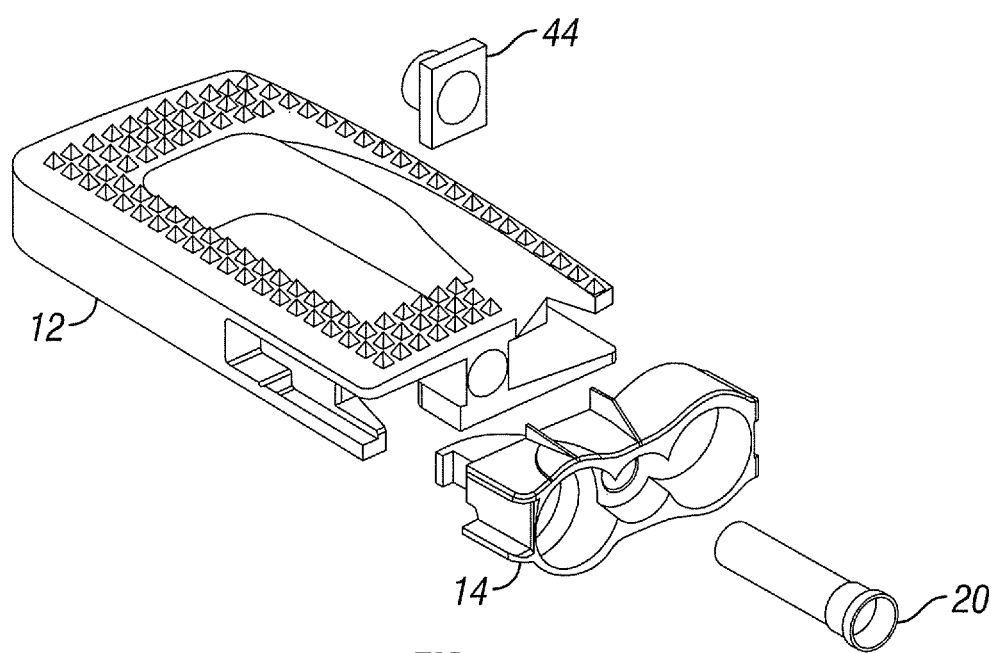
FIG. 5 is an exploded view another embodiment of the present invention.
Figure 6:
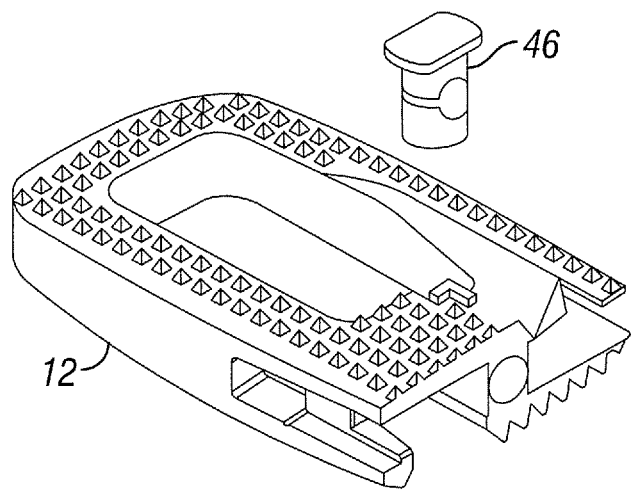
FIG. 6 is a yet another embodiment of a connection element according to the present invention.
Figure 7A:
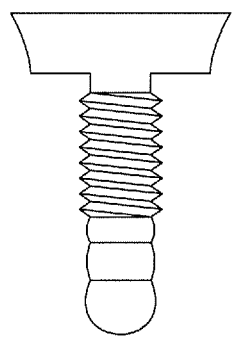
FIGS. 7A-7B, 8A-8C, and 9A-9B illustrate different embodiments for attaching the spacer portion to a plate portion of an intervertebral implant.
Figure 7B:
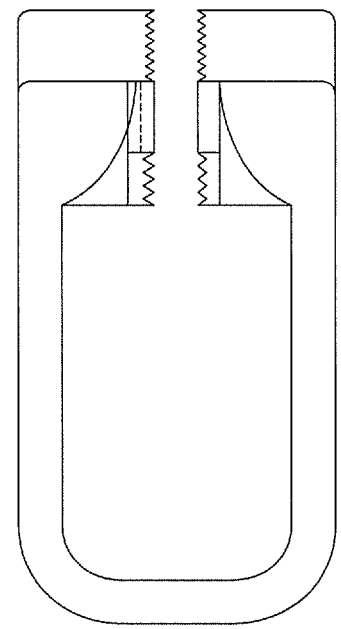

Turning back to FIG. 2, the preferred embodiment illustrates the coupling elements 20 and 22 for connecting the plate portion 14 to the spacer portion 12 of the implant 10. Specifically, the pin screw 20 is screwed into the pin hole and as the pin screw is advanced into the threaded portion of the nut 22, the spacer portion and the plate portion are securely attached. FIGS. 5 and 6 illustrate different types of nuts 44, 46 used receive and secure the pin screw to the spacer portion 12. The nut 46 illustrated in FIG. 6 is round and is provided with a mid-line feature to prevent it from backing out. The nut 46 is also flanged with flats to prevent rotation.

FIGS. 7A-7B, 8A-8C, and 9A-9B illustrate different embodiments of a mechanism to attach the plate portion to the spacer portion. FIG. 7 illustrates a plate and spacer comprising a hybrid set screw having threaded and serrated portions. The top threaded portion of the blocking set screw is configured to threaded and serrated portions. The top threaded portion of the blocking set screw may be threaded into the plate while the bottom serrated portion will ratchet into a mating female part that is positioned inside the spacer. Once the serrated portion of the set screw is actuated through threaded internal portion of the spacer, a secure single construct is created.

Figure 8A:
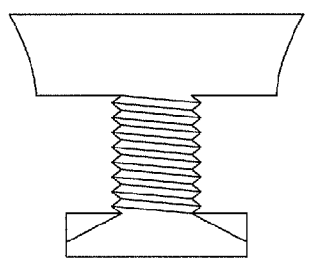
Figure 8B:
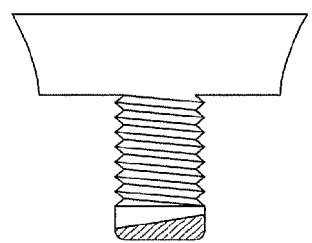
Figure 8C:
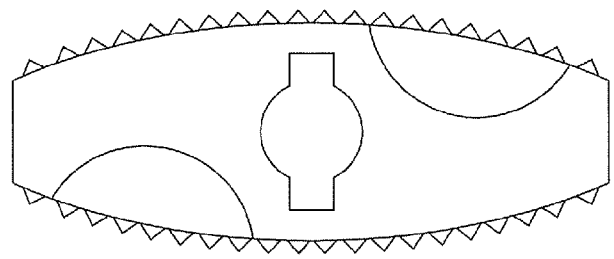

FIGS. 8A-8C illustrates yet another embodiment of a spacer and plate attached via a blocking set screw that is provided with a sloped key at it's distal tip. As the blocking set screw is rotated, the sloped key acts a cam device and clamps the spacer portion and the plate portion together. The blocking set screw may be configured and designed to have one or more sloped keys depending on the clamping force required to securely attach the spacer and the plate portions.

Figure 9A:
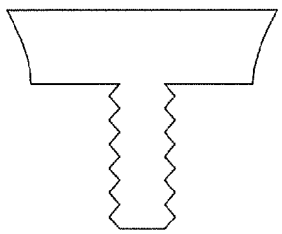
Figure 9B:
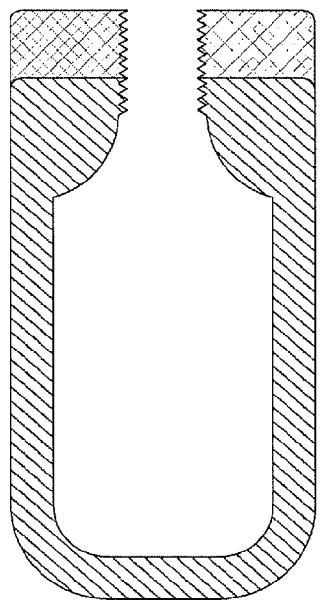

FIG. 9A-9B illustrates yet another mechanism for attaching the spacer portion to the plate portion of an intervertebral implant. In this particular embodiment, the spacer portion and the plate portion are secured via a serrated blocking screw. As the screw is screw is ratcheted through the plate and the spacer, the plate and spacer are secured together. As in the previous embodiments, the spacer portion of FIGS. 7-9 are provided with features such as superior and inferior protrusions, graft hole, and screw holes. Similarly, the plate portions of FIGS. 7-9 are also provided with screw holes for receiving bone screws that secure the spacer and plate portions to the vertebrae.

Now, turning to the method of positioning the implant, it should be noted that the intervertebral implant 10 is positioned in the spine after the disc portion between two vertebral bodies is exposed and removed using rongeurs and other suitable instruments. The posterior and anterior walls of the annulus are generally preserved to provide peripheral support for the implant and graft materials. A trial device attached to a trial holder is then inserted into the disc space to determine size of the implant. This procedure is generally conducted using fluoroscopy and tactile feel. After the appropriate sized implant is selected and attached to an implant holder and drill guide, the implant may be inserted into the disc space. As the surgeon sees fit, the spacer portion of implant may be positioned by itself or the spacer portion and the plate portion may be attached together and then positioned within the spine. If the surgeon chooses to position just the spacer portion, then the spacer portion is positioned within the disc space and graft material is used to pack the graft hole for enhancing fusion of the adjacent vertebrae. If the surgeon decides that additional support is required by attaching the plate portion to the spacer portion, the pin screw is used to attach the spacer portion to the plate portion. Once the plate and the spacer are attached, then the implant is positioned within the disc space. Next, either the combined spacer and plate or just the spacer, the implant is positioned inside the disc space, whereby an awl or any similar type of instrument can be used to drill through the screw hole and break the cortex of the adjacent vertebral body. The surgeon performing this procedure may then use a depth gauge to determine the screw length. Once the appropriate screw length is determined, screws are inserted using a self-retaining screwdriver. After the screws are finally inserted and secured thereby providing solid purchase with the adjacent vertebral bodies, the pin screw anti-back out mechanism is tightened and secured.

In another embodiment of the present invention, the plate portion is not attached to the spacer portion. The spacer portion is positioned within the disc space and bone filler material such bone graft may be delivered directly through the screw holes of the spacer portion into the graft hole. Once the bone filler material is inserted and packed within the spacer portion, a separate plate may be used or in the alternative the spacer portion can be used without the additional plate portion or any other type of plate.

While it is apparent that the invention disclosed herein is well calculated to fulfill the objects stated above, it will be appreciated that numerous modifications and embodiments may be devised by those skilled in the art.

What is claimed is:

1. An intervertebral implant for implantation in a treated area of an intervertebral space between vertebral bodies of a spine, wherein said implant comprises:
a spacer having, an inferior and superior surface, wherein the inferior and superior surfaces each have a contact area capable of engaging with anatomy in the treated area, and the inferior and superior surfaces define a graft window extending from the superior surface of the spacer to the inferior surface of the spacer;
a first screw hole extending from an anterior surface to the inferior surface of the spacer, and a second screw hole extending from the anterior surface to the superior surface of the spacer;
a plate rigidly coupled to the spacer, wherein the plate includes screws holes for receiving screws; and
wherein a screw back out prevention mechanism is adapted on the plate and prevents the back out of screws from the screw holes, wherein the posterior surface of the plate includes a first and second tongue that are configured to mate with a first and a second groove of the spacer,
wherein the screw back out prevention mechanism includes a pin screw and a nut,
wherein the nut is configured to be positioned entirely within the graft window of the spacer,
wherein the graft window is configured to receive bone graft to enhance fusion between adjacent vertebrae.

2. The intervertebral implant of claim 1, wherein the at least two screws are capable of being inserted into adjacent vertebral bodies at divergent angles.

3. The intervertebral implant of claim 1, wherein the first and second tongues are curved from a center portion of the posterior surface of the plate to a side surface of the plate and correspond to the curvature of the first and second grooves of the spacer.

4. The intervertebral implant of claim 1, wherein the plate is capable of being substantially flush with the adjacent vertebral bodies.

5. The intervertebral implant of claim 1, wherein the plate is comprised of metal.

6. The intervertebral implant of claim 5, wherein the metal is comprised of titanium.

7. The intervertebral implant of claim 1, wherein the spacer is comprised of plastic.

8. The intervertebral implant of claim 1, wherein the spacer comprises a plurality of protrusions on superior and inferior surfaces of the spacer.

9. The intervertebral implant of claim 1, wherein the nut includes a front face, a rear face, and an opening in the front face configured to receive a portion of the pin screw.

10. The intervertebral implant of claim 9, wherein the nut is recessed within the spacer and the rear face is flush with the inner surface of the spacer.

11. The intervertebral implant of claim 1, wherein a portion of the plate and the spacer are positioned between the nut and the pin screw.

12. An intervertebral implant for implantation in a treated area of an intervertebral space between vertebral bodies of a spine, wherein said implant comprises:
- a spacer having an inferior superior surface, an anterior and a posterior surface, wherein the inferior and superior surfaces each have a contact area capable of engaging with anatomy in the treated area, and the inferior and superior surfaces define a graft window extending from the superior surface of the spacer to the inferior surface of the spacer;
- a first and second hole extending from the anterior surface of the spacer to the inferior and superior surfaces of the spacer;
- a plate having an anterior and a posterior surface, the plate configured to be rigidly coupled to the spacer, wherein the plate includes a first and second hole extending from the anterior surface to the posterior surface of the plate for receiving a first and a second fastening element; and
- a fastening element of a back out prevention mechanism adapted on the plate for preventing the back out of fastening elements from the first and second holes,
- wherein a nut couples with the fastening element of the back out prevention mechanism to secure the plate to the spacer,
- wherein the nut is configured to be positioned entirely within the graft window of the spacer,
- wherein the graft window is configured to receive bone graft to enhance fusion between adjacent vertebrae.

13. The intervertebral implant of claim 12, wherein the at least two fastening elements are capable of being inserted into adjacent vertebral bodies at divergent angles.

14. The intervertebral implant of claim 12, wherein the plate comprises a tongue that mates with a first groove in the spacer portion.

15. The intervertebral implant of claim 14, wherein the tongue of the plate has a curvature and is configured to couple to the first groove of the spacer portion having a corresponding curvature.

16. The intervertebral implant of claim 15, wherein the spacer comprises a second groove for receiving a portion of an instrument, wherein the first groove and the second groove are spaced apart from one another.

17. The intervertebral implant of claim 16, wherein the plate comprises at least one groove to receive the instrument, wherein the instrument is capable of attaching to a groove of the spacer portion.

18. An intervertebral implant for implantation in a treated area of an intervertebral space between vertebral bodies of a spine, wherein said implant comprises:
- a spacer having, an inferior and superior surface, wherein the inferior and superior surfaces each have a contact area capable of engaging with anatomy in the treated area, and the inferior and superior surfaces define a graft window extending from the superior surface to the inferior surface of the spacer;
- a first and second hole extending from an anterior side of the spacer to the inferior and superior surfaces of the spacer, wherein the first and second holes are configured to receive a first and second fastener;
- a plate rigidly coupled to the spacer through a pin screw, the plate having an anterior and posterior surfaces, a first and second hole extending from the anterior surface of the plate to the posterior surface of the plate, for receiving the first and second fasteners; and
- wherein the pin screw is configured to capture sides of the first and second fasteners and couples the spacer and the plate to each other,
- a nut coupled to the pin screw and positioned on an inner surface of the spacer, wherein a portion of the plate and the spacer are positioned between the nut and the pin screw and the nut is configured to be positioned entirely within the graft window of the spacer
- wherein the graft window is configured to receive bone graft to enhance fusion between adjacent vertebrae.

19. The intervertebral implant of claim 18, wherein the spacer is formed of PEEK.

20. The intervertebral implant of claim 18, wherein the plate further comprises extensions extending from an upper surface thereof.

* * * * *